United States Patent
Keegan et al.

(10) Patent No.: US 9,375,237 B2
(45) Date of Patent: Jun. 28, 2016

(54) SYSTEM AND METHOD FOR STABILIZING VERTEBRAE IN SPINE SURGERY THROUGH A LATERAL ACCESS CHANNEL

(75) Inventors: Christopher Keegan, Hatboro, PA (US); John Ray, Albuquerque, NM (US); Jeffrey Wang, Los Angeles, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 468 days.

(21) Appl. No.: 12/679,621

(22) PCT Filed: Mar. 15, 2010

(86) PCT No.: PCT/US2010/027301
§ 371 (c)(1),
(2), (4) Date: Nov. 17, 2011

(87) PCT Pub. No.: WO2010/107692
PCT Pub. Date: Sep. 23, 2010

(65) Prior Publication Data
US 2012/0136392 A1    May 31, 2012

Related U.S. Application Data

(60) Provisional application No. 61/160,544, filed on Mar. 16, 2009, provisional application No. 61/241,705, filed on Sep. 11, 2009.

(51) Int. Cl.
| | | |
|---|---|---|
| *A61B 17/70* | (2006.01) | |
| *A61B 17/17* | (2006.01) | |
| *A61B 17/80* | (2006.01) | |
| *A61F 2/00* | (2006.01) | |
| *A61F 2/44* | (2006.01) | |
| *A61F 2/46* | (2006.01) | |
| *A61F 2/30* | (2006.01) | |

(52) U.S. Cl.
CPC ......... *A61B 17/7059* (2013.01); *A61B 17/1728* (2013.01); *A61B 17/1757* (2013.01);
(Continued)

(58) Field of Classification Search
USPC ............. 623/17, 11, 17.16; 606/86 B, 246, 606/914–916, 86 A, 99
See application file for complete search history.

(56) References Cited

U.S. PATENT DOCUMENTS

| | | | |
|---|---|---|---|
| 3,426,364 A | | 2/1969 | Lumb et al. |
| 3,661,411 A | * | 5/1972 | Flick ............................ 403/348 |

(Continued)

FOREIGN PATENT DOCUMENTS

| | | |
|---|---|---|
| EP | 0179695 A1 | 4/1986 |
| EP | 0425542 B1 | 5/1991 |

(Continued)

OTHER PUBLICATIONS http://www.thefreedictionary.com, definition of "exterior" accessed Feb. 3, 2015.*

(Continued)

*Primary Examiner* — Jan Christopher Merene
(74) *Attorney, Agent, or Firm* — Baker & Hostetler LLP

(57) ABSTRACT

A system for stabilizing a superior vertebra relative to an inferior vertebra includes a plate having a first surface for mating with the superior and inferior vertebra and a second surface opposite the first surface. The plate has a first hole configured for overlying the superior vertebra and a second hole configured for overlying the inferior vertebra. An alignment instrument has a leading portion and a trailing portion. The leading portion has a securing mechanism configured for removable attachment to a fastening mechanism of the plate. The alignment instrument also includes an alignment prong extending past the first surface of the plate when the plate is attached to the fastening mechanism. The alignment prong provides tactile information to the trailing portion of the alignment instrument for use in positioning the plate with respect to the superior and inferior vertebra.

20 Claims, 11 Drawing Sheets

(52) U.S. Cl.
CPC .............. *A61B17/808* (2013.01); *A61F 2/0095* (2013.01); *A61F 2/4465* (2013.01); *A61F 2/4611* (2013.01); *A61F 2002/30065* (2013.01); *A61F 2002/30426* (2013.01); *A61F 2002/30448* (2013.01); *A61F 2002/30507* (2013.01); *A61F 2002/30578* (2013.01); *A61F 2002/30604* (2013.01); *A61F 2002/30616* (2013.01); *A61F 2002/30841* (2013.01); *A61F 2002/30904* (2013.01); *A61F 2002/4475* (2013.01); *A61F 2002/4629* (2013.01); *A61F 2210/0071* (2013.01); *A61F 2220/005* (2013.01); *A61F 2220/0025* (2013.01)

(56) References Cited

U.S. PATENT DOCUMENTS

| | | |
|---|---|---|
| 3,867,728 A | 2/1975 | Stubstad et al. |
| 4,298,993 A | 11/1981 | Kovaleva et al. |
| 4,349,921 A | 9/1982 | Kuntz |
| 4,394,370 A | 7/1983 | Jefferies |
| 4,450,591 A | 5/1984 | Rappaport |
| 4,545,374 A | 10/1985 | Jacobson |
| 4,599,086 A | 7/1986 | Doty |
| 4,627,853 A | 12/1986 | Campbell et al. |
| 4,714,469 A | 12/1987 | Kenna |
| 4,743,256 A | 5/1988 | Brantigan |
| 4,781,721 A | 11/1988 | Grundei |
| 4,829,152 A | 5/1989 | Rostoker et al. |
| 4,834,757 A | 5/1989 | Brantigan |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,955,908 A | 9/1990 | Frey et al. |
| 4,997,432 A | 3/1991 | Keller |
| 5,006,120 A | 4/1991 | Carter |
| 5,047,058 A | 9/1991 | Roberts et al. |
| 5,116,374 A | 5/1992 | Stone |
| 5,192,327 A | 3/1993 | Brantigan |
| 5,201,736 A | 4/1993 | Strauss |
| 5,258,031 A | 11/1993 | Salib et al. |
| 5,282,861 A | 2/1994 | Kaplan |
| 5,298,254 A | 3/1994 | Prewett et al. |
| 5,306,308 A | 4/1994 | Gross et al. |
| 5,306,309 A | 4/1994 | Wagner et al. |
| 5,324,290 A | 6/1994 | Zdeblick et al. |
| 5,397,364 A | 3/1995 | Kozak et al. |
| 5,403,136 A | 4/1995 | Mathys |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,484,437 A | 1/1996 | Michelson |
| 5,522,899 A | 6/1996 | Michelson |
| 5,550,172 A | 8/1996 | Regula et al. |
| 5,556,431 A | 9/1996 | Buttner-Janz |
| 5,609,635 A | 3/1997 | Michelson |
| 5,620,448 A | 4/1997 | Puddu |
| 5,645,596 A | 7/1997 | Kim et al. |
| 5,669,909 A | 9/1997 | Zdeblick et al. |
| 5,674,296 A | 10/1997 | Bryan et al. |
| 5,683,463 A | 11/1997 | Godefroy et al. |
| 5,702,453 A * | 12/1997 | Rabbe et al. ............... 623/17.16 |
| 5,725,531 A | 3/1998 | Shapiro |
| 5,728,159 A | 3/1998 | Stroever et al. |
| 5,755,798 A | 5/1998 | Papavero et al. |
| 5,766,251 A | 6/1998 | Koshino |
| 5,766,252 A | 6/1998 | Henry et al. |
| 5,772,661 A | 6/1998 | Michelson |
| 5,782,919 A | 7/1998 | Zdeblick et al. |
| 5,836,948 A | 11/1998 | Zucherman et al. |
| 5,860,973 A | 1/1999 | Michelson |
| 5,865,845 A | 2/1999 | Thalgott |
| 5,888,223 A | 3/1999 | Bray, Jr. |
| 5,906,616 A | 5/1999 | Pavlov et al. |
| 5,964,807 A | 10/1999 | Gan et al. |
| 5,968,098 A | 10/1999 | Winslow |
| 6,001,099 A | 12/1999 | Huebner |
| 6,008,433 A | 12/1999 | Stone |
| 6,066,175 A | 5/2000 | Henderson et al. |
| 6,086,593 A | 7/2000 | Bonutti |
| 6,099,531 A | 8/2000 | Bonutti |
| 6,146,421 A | 11/2000 | Gordon et al. |
| 6,156,037 A | 12/2000 | LeHuec et al. |
| 6,206,922 B1 | 3/2001 | Zdeblick et al. |
| 6,231,610 B1 | 5/2001 | Geisler |
| 6,235,059 B1 | 5/2001 | Benezech et al. |
| 6,258,089 B1 | 7/2001 | Campbell et al. |
| 6,364,880 B1 | 4/2002 | Michelson |
| 6,432,106 B1 | 8/2002 | Fraser |
| 6,443,987 B1 | 9/2002 | Bryan |
| 6,482,233 B1 | 11/2002 | Aebi et al. |
| 6,511,509 B1 | 1/2003 | Ford et al. |
| 6,540,785 B1 | 4/2003 | Gill et al. |
| 6,623,486 B1 | 9/2003 | Weaver et al. |
| 6,626,907 B2 | 9/2003 | Campbell et al. |
| 6,916,320 B2 | 7/2005 | Michelson |
| 6,989,012 B2 | 1/2006 | LeHuec et al. |
| 7,048,765 B1 | 5/2006 | Grooms et al. |
| 7,074,221 B2 | 7/2006 | Michelson |
| 7,128,744 B2 | 10/2006 | Weaver et al. |
| 7,238,203 B2 * | 7/2007 | Bagga et al. ............... 623/17.11 |
| 8,444,696 B2 | 5/2013 | Michelson |
| 2002/0004683 A1 | 1/2002 | Michelson |
| 2002/0087212 A1 | 7/2002 | James et al. |
| 2002/0193880 A1 | 12/2002 | Fraser |
| 2003/0125739 A1* | 7/2003 | Bagga et al. ............... 606/61 |
| 2003/0199881 A1 | 10/2003 | Bonutti |
| 2005/0085913 A1* | 4/2005 | Fraser et al. ............... 623/17.11 |
| 2005/0187552 A1 | 8/2005 | Michelson |
| 2006/0189997 A1 | 8/2006 | Guenther et al. |
| 2006/0229618 A1 | 10/2006 | Dube |
| 2006/0235403 A1* | 10/2006 | Blain ............... 606/69 |
| 2007/0270965 A1* | 11/2007 | Ferguson ............... 623/17.11 |
| 2008/0161925 A1* | 7/2008 | Brittan et al. ............... 623/17.16 |
| 2008/0294262 A1* | 11/2008 | Levieux ............... 623/17.16 |
| 2008/0300634 A1* | 12/2008 | Gray ............... 606/280 |
| 2009/0012529 A1 | 1/2009 | Blain et al. |
| 2009/0024132 A1* | 1/2009 | Blain et al. ............... 606/96 |
| 2010/0100138 A1* | 4/2010 | Reynolds et al. ............... 606/86 A |
| 2010/0152853 A1* | 6/2010 | Kirschman ............... 623/17.11 |
| 2010/0228297 A1* | 9/2010 | Bray et al. ............... 606/279 |

FOREIGN PATENT DOCUMENTS

| | | |
|---|---|---|
| EP | 0641547 B1 | 3/1995 |
| EP | 1103236 B1 | 8/2006 |
| FR | 2703580 A1 | 10/1994 |
| FR | 2727003 | 5/1996 |
| FR | 2747034 | 10/1997 |
| WO | WO 89/09035 | 10/1989 |
| WO | WO 90/00037 | 1/1990 |
| WO | WO 93/01771 | 2/1993 |
| WO | WO 95/08964 | 4/1995 |
| WO | WO 95/15133 | 6/1995 |
| WO | WO 95/20370 | 8/1995 |
| WO | WO 95/26164 | 10/1995 |
| WO | WO 96/40015 | 12/1996 |
| WO | WO 97/20526 | 6/1997 |
| WO | WO 97/37620 | 10/1997 |
| WO | WO 98/17208 | 4/1998 |
| WO | WO 98/17209 | 4/1998 |
| WO | WO 99/09896 | 3/1999 |
| WO | WO 99/38463 | 8/1999 |
| WO | WO 99/63914 | 12/1999 |

OTHER PUBLICATIONS

ATB Anterior Tension Band Plate, Surgical Technique Guide, Synthes GmbH, Nov. 2010, 28 pages.
Antegra Instruments and Implants, Technique Guide, Synthes Spine, 2007, 29 pages.
U.S. Appl. No. 60/068,205, filed Dec. 19, 1997, Urbahns.

(56) References Cited

OTHER PUBLICATIONS

U.S. Appl. No. 60/071,527, filed Jan. 15, 1998k Urbahns.
Synthes History and Evolution of LBIF Brochure; Nov. 2015, 30 pages.
Synthes Spine Cervical Stand-Alone Devices Presentation Brochure; 2010, 40 pages.
DePuy Motech Surgical Titanium Mesh Brochure; 1998, 13 pages.
AcroMed Carbon Fiber Interbody Fusion Devices; Jan. 1998, 8 pages.
Carbon Fiber Composite Ramps for Lumbar Interbody Fusion; Apr. 1997, 2 pages.
Al-Sanabani, Application of Calcium Phosphate Materials in Dentistry, vol. 2013, Int. J. Biomaterials, 1-12, 2013.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20(9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan I/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No, 300, Clin. Orth. Rel. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117, 2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical,16(S2) Neurochirurgie 1-212; 1970 (w/Translation).
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.
Dabrowski, Highly Porous Titanium Scaffolds for Orthopaedic Applications, J. Biomed Mater. Res. B. Appl. Biomat. Oct;95(1):53-61, 2010.
Takahama, A New Improved Biodegradable Tracheal Prosthesis Using Hydroxy Apatite and Carbon Fiber 35(3) ASAIO Trans, 291-293, Jul.-Sep. 1989.
Wang, Determination of Cortical Bone Porosity and Pore Size Distribution using a Low Field Pulsed NMR Approach, J. Orthop Res., Mar; 21(2):312-9 Mar. 2003.

* cited by examiner

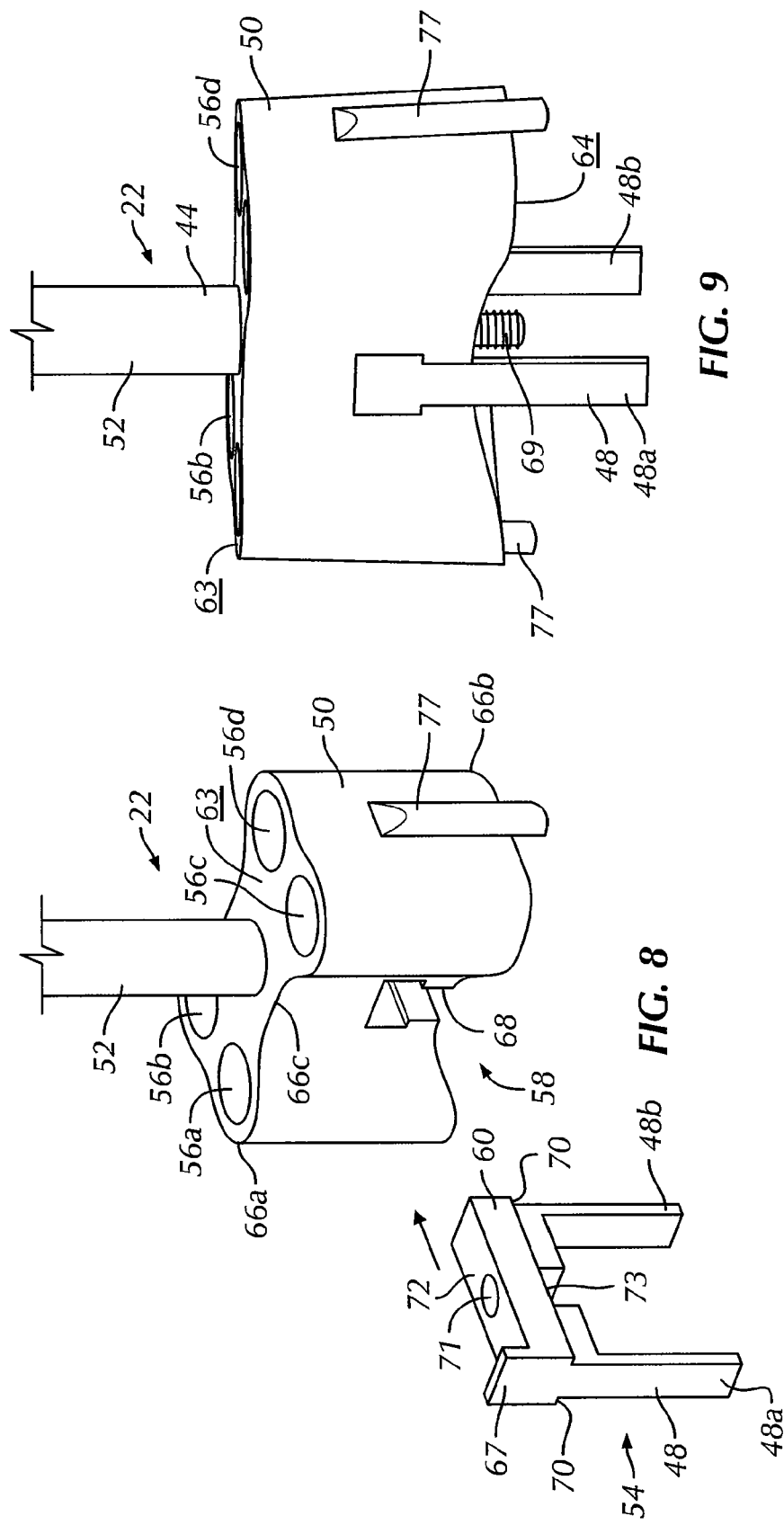

SYSTEM AND METHOD FOR STABILIZING VERTEBRAE IN SPINE SURGERY THROUGH A LATERAL ACCESS CHANNEL

CROSS-REFERENCE TO RELATED APPLICATIONS

This application is a National Stage of International Application No. PCT/US2010/027301, filed Mar. 15, 2010, which claims the benefit of U.S. Provisional Application No. 61/160,544 filed Mar. 16, 2009, and U.S. Provisional Application No. 61/241,705, filed Sep. 11, 2009, the disclosure of each of which is incorporated herein by reference.

BACKGROUND

The present device relates generally to a system and method for stabilizing vertebrae and, more particularly, to a system and method for optimally aligning and/or attaching a plate with respect to a spacer during spine surgery to stabilize vertebrae.

Interbody spacers and spinal plate assemblies are utilized to restore disc height, allowing fusion to occur between two adjacent vertebral bodies, and provide stability during the fusion process. The plate may be mechanically coupled to the spacer to provide implant stability during healing, reduction in the number of surgical steps, as well as to orient the trajectory of a plurality of bone anchors during implantation. Surgical techniques involving lateral access to the lumbar spine have reduced risks to the patient inherent to anterior or posterior access, but lateral implant of a spacer and plate conventionally requires the spacer and plate to be mechanically coupled for proper alignment.

It is desirable to optimally align the plate with respect to the spacer without mechanically coupling the plate to the spacer, especially when performing surgery through a lateral access channel to the lumbar spine, where a large amount of tissue is retracted and visualization may be limited. However, such optimal alignment can be difficult to achieve.

BRIEF SUMMARY

Briefly stated, one aspect of the exemplary device is directed to a system for stabilizing a superior vertebra relative to an inferior vertebra. The superior vertebra and inferior vertebra have a spacer positioned therebetween. A plate has a first surface configured for mating with the superior and inferior vertebra and a second surface generally opposite the first surface. The plate has a first hole between the first and second surface and a second hole between the first and second surface. The first hole is configured for overlying the superior vertebra and the second hole is configured for overlying the inferior vertebra. The plate further includes a fastening mechanism. An alignment instrument has a leading portion and a trailing portion. The leading portion has a securing mechanism configured for removable attachment to the fastening mechanism of the plate. The alignment instrument also includes an alignment prong extending past the first surface of the plate when the plate is attached to the fastening mechanism. The alignment prong provides tactile information to the trailing portion of the alignment instrument for use in positioning the plate with respect to the superior and inferior vertebra.

Another aspect is directed to a method for stabilizing a superior vertebra relative to an inferior vertebra in spine surgery through a lateral access channel. The method includes inserting a spacer into a disc space between the superior and inferior vertebrae. The spacer has a distal end, a proximal end, a first side surface and a second side surface. The first side surface has a slot formed therein adjacent the proximal end. The method includes attaching a leading end of an alignment instrument to a proximal surface of a plate. An alignment prong extends outwardly beyond the leading end of the alignment instrument and beyond the distal surface of the plate when the leading end and proximal surface are attached. The method includes using the alignment instrument to align the plate with respect to the spacer by inserting at least a portion of the alignment prong into at least a portion of the slot of the spacer. The method includes inserting at least one screw through the plate and into the superior vertebra and inserting at least another screw through the plate into the inferior vertebra to fixedly attach the plate to the superior and inferior vertebrae. The method also includes the step of separating and withdrawing the leading end of the alignment instrument from the plate.

BRIEF DESCRIPTION OF THE SEVERAL VIEWS OF THE DRAWINGS

The foregoing summary, as well as the following detailed description of the device and method, will be better understood when read in conjunction with the appended drawings. For the purpose of illustrating the device and method of the present application, there is shown in the drawings exemplary embodiments. It should be understood, however, that the exemplary device and method are not limited to the precise arrangements and instrumentalities shown. In the drawings:

FIG. 8 is a side isometric view of the shaft and the aiming device shown in a spaced-apart configuration from a locating guide of the alignment instrument, as shown in FIGS. 1-3, 6 and 7;

FIG. 9 is a side isometric view of the shaft, the aiming device and the locating guide shown in FIG. 8 in an assembled configuration to form the assembled alignment instrument;

DETAILED DESCRIPTION

Figure 1A:
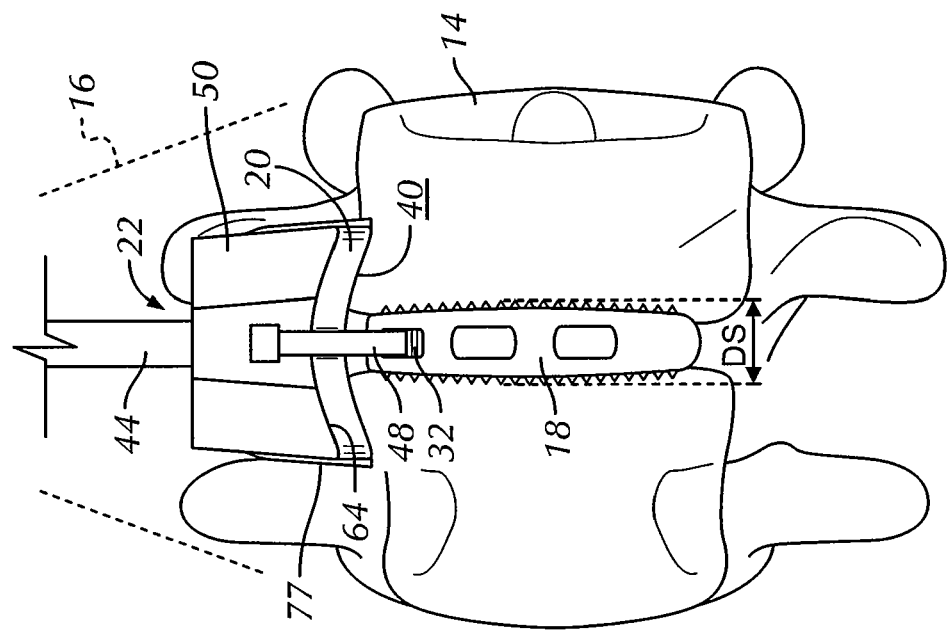
FIG. 1A is a magnified anterior elevational view of a portion of FIG. 1.
Figure 1:
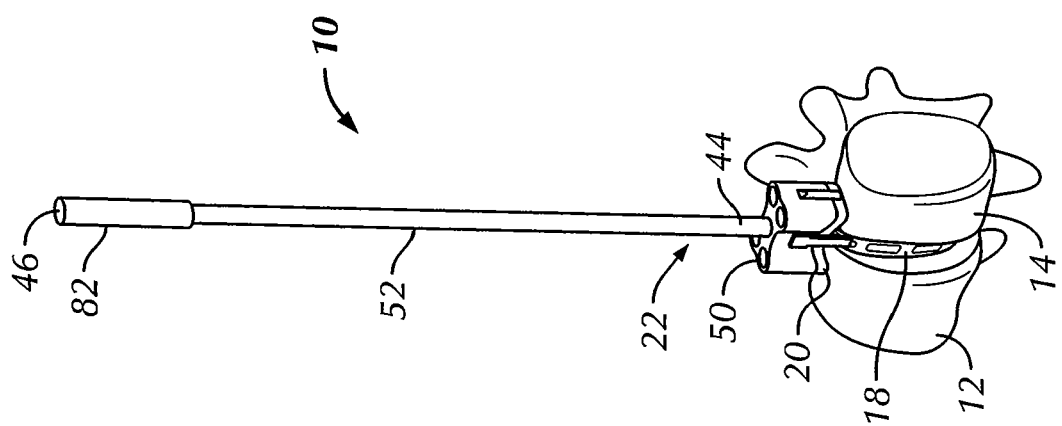
FIG. 1 is an isometric view of a plate being aligned relative to adjacent vertebrae and a spacer using an alignment instrument according to an exemplary embodiment of the present application.

Certain terminology is used in the following description for convenience only and is not limiting. The words "right," "left," "lower," "upper," "top," "bottom," "middle," "proximal" and "distal" designate directions in the drawings to which reference is made. The words "inwardly" and "outwardly" refer to directions toward and away from, respectively, the geometric center of the patient, vertebra, spacer, plate or alignment instrument, and designated parts thereof. The words, "anterior," "posterior," "superior," "inferior," "lateral," "medial," and related words and/or phrases designate exemplary positions and orientations in the human body to which reference is made and are not meant to be limiting. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, there is shown in FIGS. 1-18 a system, generally designated 10, for stabilizing a superior vertebra 12 relative to an inferior vertebra 14 in spine surgery, through a lateral access channel 16 (shown in phantom in FIG. 1A). Although reference herein is made to a system 10 having a plurality of separate parts and/or components that allow a surgeon to optimally align and/or attach a spinal plate to a vertebral spacer and/or one or more vertebrae, the system 10 is not limited to the inclusion of each component and may accomplish the intended function of stabilizing vertebrae 12, 14 using fewer or more components. Specifically, in a first exemplary embodiment, the system 10 generally includes at least one interbody spacer 18, at least one vertebral fixation plate 20 and at least one alignment instrument 22. However, the system 10 is not limited to the inclusion of the above-indentified components, as more or fewer components may constitute "the system 10" to achieve the desired function of stabilizing adjacent vertebrae 12, 14 to permit fusion between the vertebrae 12, 14.

The spacer 18, the plate 20 and the alignment instrument 22 are configured for use in lateral surgeries to the lumbar spine, such as extraforaminal posterior, trans-psoatic, and anterolateral approaches to fuse lumbar vertebrae. While the spacer 18, the plate 20 and the alignment instrument 22 are typically configured for lateral lumbar applications, the components of the system 10 may be adapted for a variety of spacer and plate configurations and indications, such as anterior cervical plates and spacers, lateral thoracic spacers, or the like.

Figure 10:
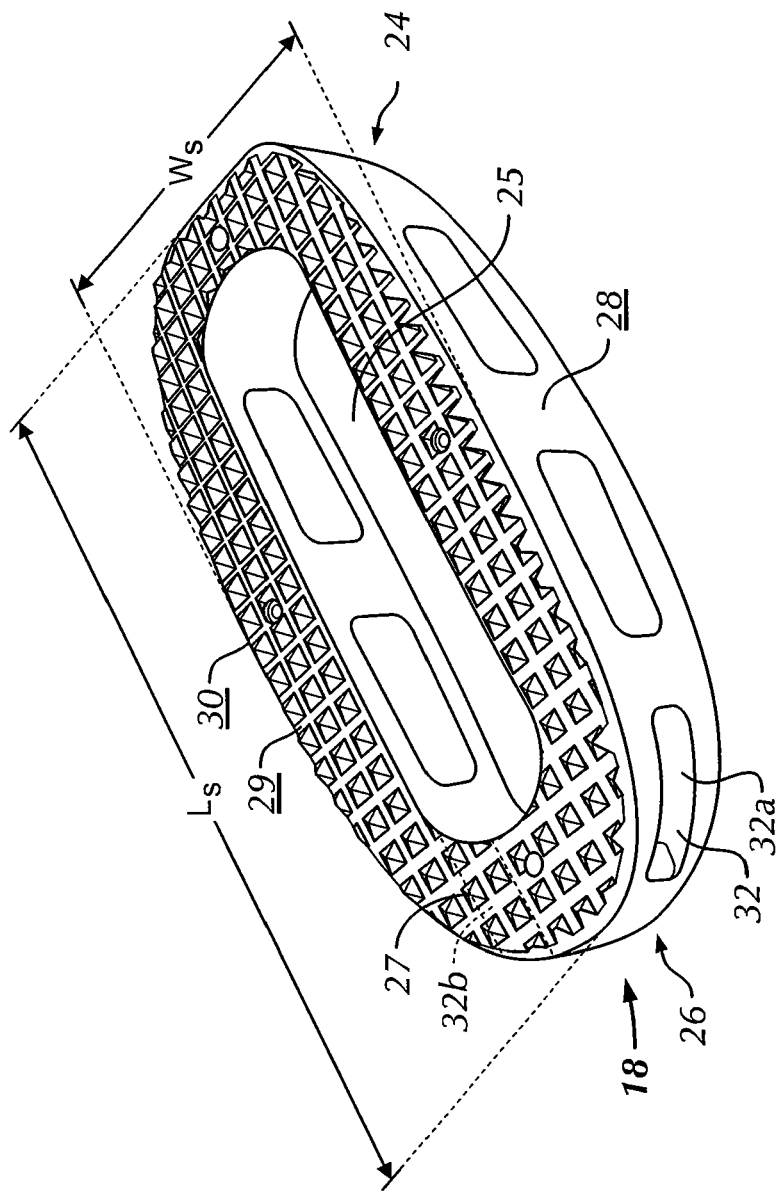
FIG. 10 is a top isometric view of the spacer shown in FIGS. 1-3.

Referring to FIGS. 1-3, 10, 11, 14, 16 and 18, an exemplary embodiment of the spacer 18 is sized and shaped to generally fit entirely within a disc space DS (FIG. 1A) in an implanted configuration (FIGS. 1-3, 14, 16 and 18). The spacer 18 generally includes a distal or leading end 24, an opposing proximal or trailing end 26, a first or right side surface 28, an opposing second or left side surface 30, a third or top surface 29 and an opposing fourth or bottom surface 31. In the first exemplary embodiment, the first side surface 28 includes one ore more engagement features or slots 32 formed therein at least generally adjacent the proximal end 26. More specifically, the proximal end 26 typically includes two spaced-apart slots 32 located on either side of a longitudinal axis of the spacer 18 that extend along the side surfaces 28, 30 and are exposed or open at the proximal end 26. For example, as seen in FIG. 10, the spacer 18 generally includes a first slot 32a on or in the first side surface 28 adjacent the proximal end 26 and a second slot 32b on or in the second side surface 30 adjacent the proximal end 26. The spacer 18 also typically includes a central opening 25 for housing bone graft material (not shown) and providing a path for boney fusion to occur through the spacer 18. The spacer 18 may be formed from a range of biocompatible materials, such as metals, including stainless steel and titanium, polymers, such as polyether ether ketone (PEEK), composite materials, allograft bone, or the like.

Figures 11, 12:
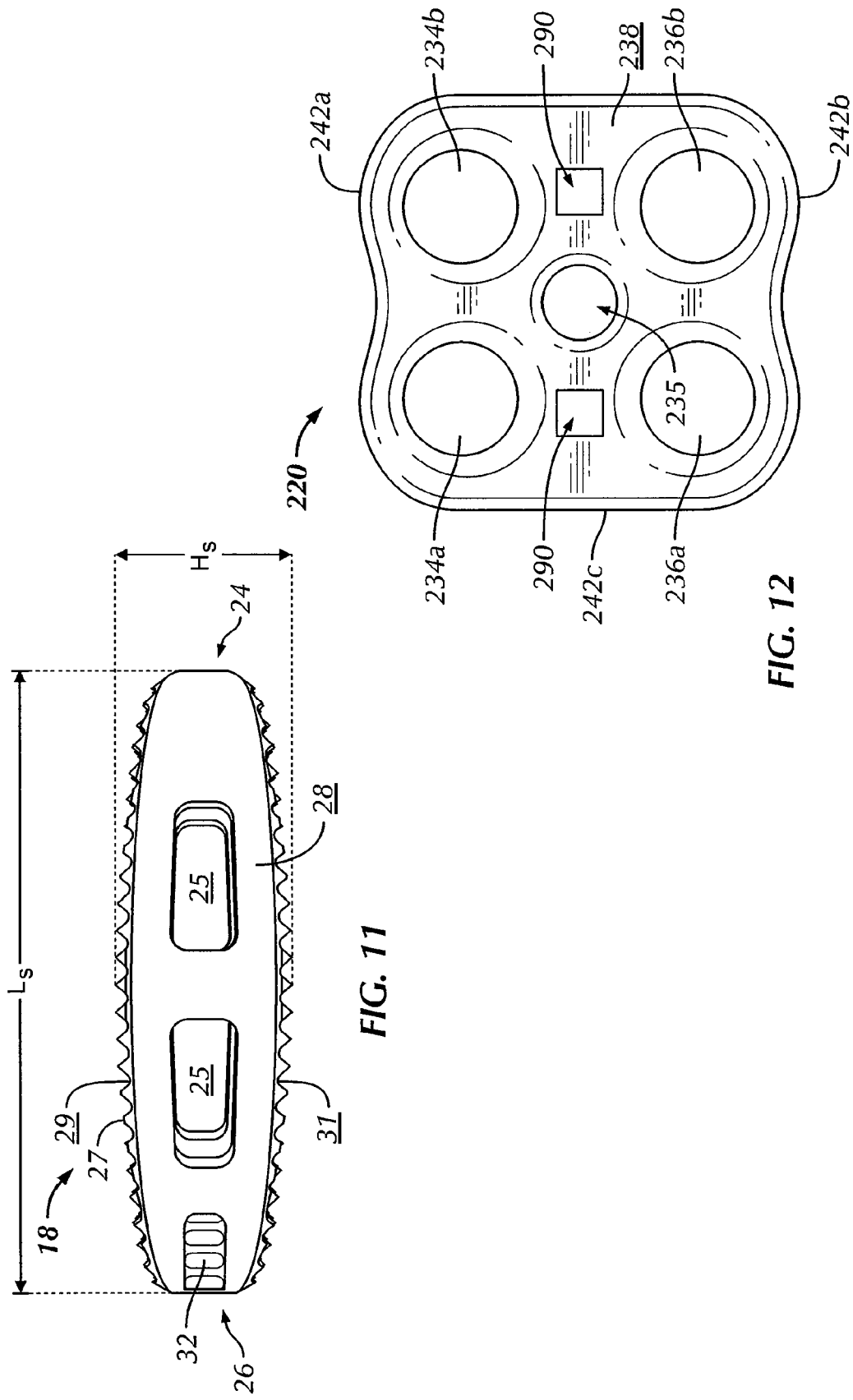
FIG. 11 is a side elevational view of the spacer shown in FIG. 10.
FIG. 12 is a top plan view of a plate in accordance with a second exemplary embodiment of the present application.

As seen in FIGS. 10 and 11, the spacer 18 has a spacer length $L_S$, as measured along the longitudinal axis of the spacer 18 from the furthest point of the proximal end 26 to the furthest point of the distal end 24, and a spacer width $W_S$, as measured along an axis perpendicular to the longitudinal axis of the spacer 18 from the furthest point of the right side surface 28 to the furthest point of the left side surface 30. The spacer 18 also generally includes a spacer height $H_S$, as measured along an axis perpendicular to the longitudinal axis from the highest point of the top surface 29 to the lowest point of the bottom surface 31.

In the exemplary embodiment, the spacer length $L_S$ is significantly greater than the spacer width $W_S$, which are both greater than the spacer height $H_S$. However, the spacer length $L_S$ may be approximately two or more times greater than the spacer width $W_S$. For example, the spacer length $L_S$ may be approximately thirty eight to fifty millimeters (38-50 mm) and the spacer width $W_S$ may be approximately eighteen to twenty millimeters (18-20 mm). However, the spacer 18 is not limited to having the above-described length and width ranges, and may include other appropriate footprints and various heights in the ranges including, but not limited to, seven to seventeen millimeters (7-17 mm) for the spacer height $H_S$. The spacer 18 may be manufactured in other dimensions as well.

The distal end 24 of the spacer 18 typically includes a tapered or bullet-shaped nose to ease insertion of the spacer 18 into the disc space DS between adjacent vertebrae 12, 14. In addition, one or both of the top and bottom surfaces 29, 31 of the spacer 120 are generally at least partially rough to engage the respective vertebrae 12, 14 to initially secure the spacer 18 to the vertebrae 12, 14. Specifically, the entire top and bottom surfaces 29, 31 typically include a plurality of spaced-apart projections or teeth 27, which may be in the shape of a pyramid or saw-tooth, for example. The teeth 27 may also be serrated to inhibit backing-out of the spacer 18 from the disc spacer DS. The teeth 27 may have, for example, a height of approximately one millimeter (1 mm). The top and bottom surfaces 29, 31 may further be convexly shaped along the spacer length $L_S$ to conform to the patient's anatomy. Alternatively or additionally, the top and bottom surfaces 29, 31 may be convex in both the anterior-posterior plane as well as in the sagittal plane. Further, the top and bottom surfaces 29, 31 may take on a lordotic or wedge-shape to generally adapt to the anatomic positioning of the adjacent vertebrae 12, 14. For example, the top and bottom surfaces 29, 31 may be formed with a radius of curvature of two hundred millimeters (200 mm) in the anterior-posterior plane and fifty millimeters (50 mm) in the sagittal plane, for example.

FIGS. 1-5 show the plate 20 in accordance with a first exemplary embodiment that is sized and shaped to be fixedly attach to at least one but typically both the superior and inferior vertebrae 12, 14 in the implanted configuration near the proximal end 26 of the spacer 18. Further, the plate 20 is generally configured to span the disc space DS into which the spacer 18 is implanted. The plate 20 includes a proximal or second surface 38 (FIG. 4) and an opposing distal or first surface 40 (FIG. 1A). The distal surface 40 generally faces and/or engages at least a portion both the superior and inferior vertebrae 12, 14 in the implanted configuration and the spacer 20 has a predetermined thickness such that the distal or first surface 40 is spaced a predetermined distance from the proximal surface 38 of the spacer 18 in the implanted configuration. At least the distal surface 40 often includes a surface geometry that is configured to match the anatomy of the lateral aspects of the adjacent vertebrae 12, 14. Thus, at least the distal surface 40 is generally at least slightly concave in shape. Further, the proximal surface 38 may be convexly shaped (see FIGS. 1A-3), flat or planar.

Figure 4:
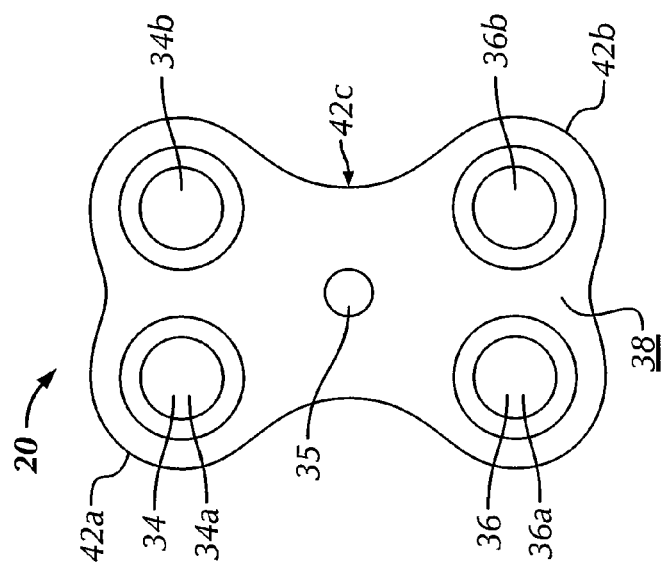
FIG. 4 is a top plan view of the plate shown in FIGS. 1-3.

As seen in FIG. 4, the plate 20 typically has at least one superior or first screw hole 34 and at least one inferior or second screw hole 36. In the first exemplary embodiment, the superior screw hole 34 includes a first or upper-left side screw hole 34a spaced a predetermined distance apart from a second or upper-right side screw hole 34b. Further, the inferior screw hole 36 typically includes a third or lower-left side screw hole 36a spaced a predetermined distance apart from a fourth or lower-right side screw hole 36b. Each screw hole 34, 36 is sized and shaped to receive a bone anchor or screw 62 therethrough to secure the plate 20 to the adjacent vertebrae 12, 14 in the implanted configuration. Each screw hole 34, 36 may include a generally smooth interior wall, or the interior wall may include a series of screw threads (not shown) to engage threads of the bone anchor 62. The interior walls of the screw holes 34, 36 may also include features, which are known to those having ordinary skill in the art, to prevent back-out of the screws 62.

Referring again to FIG. 4, in the first exemplary embodiment, the plate 20 typically includes a superior or first portion 42a, an opposite inferior or second portion 42b, and a middle portion or neck 42c located between the superior and inferior portions 42a, 42b. More specifically, the neck 42c is generally located between the superior and inferior screw holes, 34, 36. T neck 42c generally has a narrower width than either the superior or inferior portions 42a, 42b and that opposing sides of the plate 20 have a generally smooth contour or shape defining a concave surface at the neck 42c between the superior and inferior portions 42a, 42b. Thus, the plate 20 typically has a hour-glass or dog-bone shape when viewed from above or below (i.e., FIG. 4), but the plate 20 is not so limited. Further, a superior side (i.e., top side) of the plate 20, proximate the superior portion 42a, and an inferior side (i.e., bottom side) of the plate 20, proximate the inferior portion 42b, are generally slightly curved, non-linear or concave. However, the concave shapes of the superior and inferior sides of the plate 20 are generally less pronounced or of a lesser degree than the concave shape of the opposing sides of the plate 20 proximate the neck 42c. The plate 20 may also include at least one hole or fastening mechanism 35 that is threaded and at least generally centrally disposed within the plate 20. The hole 35 typically extends at least partially through the proximal surface 38 of the plate 20 and extends completely through the plate 20 from the proximal or second surface 38 to the distal or first surface 40. The fastening mechanism 35 is not limited to a threaded hole 35 as is shown and described for the first exemplary embodiment and may be comprised of any mechanism that permits releasable securing of the plate 20 to the alignment instrument 22, such as clamps, magnetic devices, adhesives, prongs or other mechanisms that permit releasable engagement of the alignment instrument 22 to the plate 20.

Referring to FIGS. 1-2 and 6-9, a first exemplary embodiment of the alignment instrument 22 includes a shaft 52 having a leading or distal end 44 and an opposing trailing or proximal end 46. As described in detail below, the leading end 44 of the shaft 52 is generally sized and shaped for removable attachment to the plate 20. The alignment instrument 22 typically includes an alignment prong 48 that extends outwardly therefrom and is generally sized and shaped to be positioned at least partially within the slot 32 of the spacer 18 in an insertion position such that the plate 20 is aligned with respect to the spacer 18 for attachment to the superior and inferior vertebrae 12, 14. In addition, a portion of the distal end 44 of the shaft 52 includes a series of screw threads or a securing mechanism 69 that are typically sized and shaped to matingly engage at least a portion of the hole or fastening mechanism 35 of the plate 20. The securing mechanism 69 is not limited to being comprised of the series of screw threads 69 and may be comprised of nearly any mechanism that permits releasable engagement of the shaft 52 to the plate 20. For example, the securing mechanism may be comprised of a clamp, magnetic mechanism, adhesives, bayonet lock or any mechanism that permits releasable engagement of the shaft 52 to the plate 20.

In the first exemplary embodiment, the alignment instrument 22 also includes an aiming device 50 located generally proximate or at the distal end 44 of the shaft 52 in an assembled configuration. More specifically, the distal end 44 of the shaft 52 is selectively, removably attachable to the aiming device 50. A distal surface 64 (FIG. 9) of the aiming device 50 has at least generally the same or a mating version of the size, shape and cross-sectional area of the proximal surface 40 of the plate 20. A proximal surface 63 (FIGS. 8 and 9) of the aiming device 50, which generally opposes the distal surface 64 and is spaced a predetermined distance therefrom, has generally the same cross-sectional area as the distal surface 64 of the aiming device 50. The proximal surface 63 is generally flat or planar, but the size and shape of the proximal and distal surfaces 63, 64 are not limited to the specifications described above. Further, a thickness of the aiming device 50, as measured from the proximal to distal surfaces 63, 64 is substantially greater, such as by three times the thickness of the plate 20, as measured from the proximal to distal surfaces 38, 40 thereof. Similar to the plate 20, it is typical that the aiming device 50 includes a superior or first portion 66a, an opposite inferior or second portion 66b, and a middle portion or neck 66c. Like the plate 20, the aiming device 50 generally has an hour glass or dog-bone shape when viewed from above or below (generally FIGS. 6 and 7). A passageway or opening 78, which is threaded, extends completely through the aiming device 50, such as from the proximal to the distal surfaces 63, 64, generally at the neck 22.

As seen in FIGS. 1A, 2, 8 and 9, the aiming device 50 generally includes at least one and often two spaced-apart and diametrically opposed extensions 77. In the first exemplary embodiment, one extension 77 is located proximate the superior portion 66a and a second extension 77 is located proximate the inferior portion 66b of the aiming device 50. Further, at least a portion of each extension 77 extends beyond the distal surface 64 of the aiming device 50, such as by a distance generally equal to the thickness of the plate 20. The extensions 77 typically allow a surgeon or other user to properly align the aiming device 50 with respect to the plate 20 during assembly. Specifically, each extension 77 is sized and shaped to engage or fit within the slightly concave shape of the superior and inferior sides of the plate 20 Additionally, the extensions 77 prevent rotational movement of the plate 20 with respect to the aiming device 50 when the shaft 52 is being inserted through the passageway 78 of the aiming device 50 and the hole 35 of the plate 20.

Referring to FIGS. 8 and 9, the aiming device 50 of the alignment instrument 22 generally includes first, second, third and fourth alignment bores 56a-56d that extend from the proximal surface 63 to the distal surface 64 thereof. The first, second, third and fourth alignment bores 56a-56d are generally sized and shaped to align with the first, second, third and fourth screw holes 34a, 34b, 36a, 36b, respectively, of the plate 20 in the assembled configuration and the insertion position. The aiming device 50 also typically includes a guide groove 58 (FIG. 8) proximate to or at the neck 66c and the distal surface 64 thereof. The guide groove 58 extends from the distal surface 64 of the aiming device 50 into an interior thereof and the entire width of the neck 42c. Two generally opposing flanges 68 extend inwardly into an interior of the guide groove 58 to define a narrowed portion of the guide groove 58. Thus, the aiming device 50 serves as a drill guide to ensure proper trajectory for drilling and insertion of the screws 62 to secure the plate 20 to the vertebrae 12, 14. The alignment bores 56a-56d of the aiming device 50 are generally located and angled to guide the screws 62 into generally the hardest or most dense portion of each vertebra 12, 14 to establish a secure connection with the vertebrae 12, 14. Specifically, the alignment bores 56a-56d are positioned and oriented to guide each screw 62 into a region of each vertebra 12, 14 generally proximate the corners of the vertebrae 12, 14 and at or near the endplates of the vertebrae 12, 14, but not through the endplates such that a distal end of a screw 62 extends outwardly beyond the endplate.

In addition, the alignment instrument 22 often includes a locating guide 54 that is sized and shaped to be selectably removably attachable to the aiming device 50. Specifically, the locating guide 54 typically has a base arm 60 selectively mountable in the guide groove 58 of the aiming device 50. A pair of flanges 70 extend outwardly from opposing sidewalls of the base arm 60 and are sized and shaped to matingly engage with the flanges 68 of the guide grove 58 of the aiming device 50. Further, a passageway or hole 71, which is threaded, extends from a proximal surface 72 to a distal surface 73 of the base arm 60. The passageway 71 is sized and shaped to selectively engage the screw threads 69 of the distal end 44 of the shaft 52. A lip 67 (FIG. 8) extends outwardly from a portion of the base arm 60 to prevent the locating guide 54 from sliding completely through the guide groove 58.

Engagement of the screw threads 69 of the shaft 52 with the passageway 71 of the locating guide 54 generally locks the locating guide 54 with respect to the aiming device 50 and the shaft 52, and generally prevents inadvertent rotational movement of the locating guide 54 with respect to the shaft 52 when the base arm 60 is positioned within the guide groove 58. However, the locating guide 54 may be integral and unitary with, and thus permanently attached to, the locating guide 54 and/or alignment instrument 22. A handle or knob 82 at the proximal end 46 of the shaft 52 typically allows the screw threads 69 at the distal end 44 to be advanced or withdrawn within the hole 35 of the plate 20, the passageway 78 of the aiming device 50, and the passageway 71 of the base arm 60 of the locating device 54.

In the first exemplary embodiment, the locating guide 54 includes the alignment prong 48 thereon. In other words, the alignment prong 48 forms at least part of the locating guide 54. Furthermore, the alignment prong 48 includes a first alignment prong 48a spaced a predetermined distance apart from a second alignment prong 48b. The first and second alignment prongs 48a, 48b are typically sized and shaped to be positioned adjacent the neck 42 of the plate 20 in the insertion position. Further, the first alignment prong 48a of the alignment instrument 22 is generally positioned at least partially within the first slot 32a of the spacer 18 and the second alignment prong 48b is positioned at least partially within the second slot 32b in the insertion position. In the assembled configuration, the first and second alignment prongs 48a, 48b extend axially away from the first or distal surface 40 of the plate 20 approximately five to ten millimeters (5-10 mm), but are not so limited. The first and second alignment prongs 48a, 48b may extend a shorter distance, such as two millimeters (2 mm) or three millimeters (3 mm), from the distal surface 40 for relatively small spacers 18 or may extend a greater distance, such as eleven millimeters (11 mm) or twenty millimeters (20 mm), from the distal surface 40 to engage relatively long slots 32 in the spacer 18 or for relatively large spacers 18. In the first exemplary embodiment, the first and second alignment prongs 48a, 48b extend approximately seven and one-half millimeters (7.5 mm) away from the first or distal surface 40 of the plate 20 in the assembled configuration. The first and second alignment prongs 48a, 48b are not limited to extending from the first or distal surface 40 at the above-described distances and may extend from the distal surface 40 to nearly any length or distance that provides tactile feedback to the surgeon at the 52

In operation, an incision is initially made in a patient's side and the access channel 16 is formed to provided access to the spinal disc space DS in need of repair. An at least partial discectomy is performed on the disc space DS and the spacer 18 is then inserted between the adjacent vertebrae 12, 14 with the distal end 24 entering the disc space DS first such that once the spacer 18 is in a desired position within the disc space DS, the proximal end 26 is proximate the incision and access channel 16. The distal end 44 of the shaft 52 is then coupled to the aiming device 50, and then the combined shaft and aiming device 50 is coupled to the plate 20, as described in detail above. Alternatively, the locating guide 54 is coupled to the combined aiming device 50 and shaft 52 before engagement with the plate 20, as described above, to form the assembled alignment instrument 22. In addition, the locating guide 54 may be coupled to the aiming device 50 before the aiming device 50 is coupled to the shaft 52. A single locating guide 54 may be used with each of the aiming devices 50 of a kit or each aiming device 50 may be associated with a different locating device 54.

Next, the plate 20 is coupled to the assembled alignment instrument 22, by inserting the distal end of the shaft 52 into the hole 35 of the plate 20. In this configuration, at least a portion of both of the extensions 77 of the aiming device 50 and the alignment prongs 48a, 48b of the locating guide 54 surround at least a portion of the plate 20. The assembled alignment instrument 22 is then used to insert the plate 20 down the access channel 16 and position the plate 20 with respect to the implanted spacer 18 by mating the alignment prongs 48a, 48b, which protrude beyond the distal surface 40 of the plate 20, with the slots 32a, 32b of the spacer 18. Once the one or more alignment prongs 48 are mated to the one or more slots 32, the plurality of screws 62 are driven into the adjacent vertebrae 12, 14 through the screw holes 34, 36 of the plate 20 and the alignment bores 56a-56d of the aiming device 50 using a screwdriver 65, drill or other driver instrument. The relatively long alignment bores 56a-56d of the aiming device 50 assist the surgeon in setting the trajectory of the screws 62 into the vertebrae 12, 14 to optimize position and alignment of the screws 62 relative to the spacer 18 and the vertebrae 12, 14.

Once the screws 62 are inserted through the screw holes 34, 36 of the plate 20 and into the adjacent vertebrae 12, 14, the shaft 52 is unscrewed from the hole 35 of the plate 20. At this point, the plate 20 is fixedly coupled to the vertebrae 12, 14. The assembled alignment instrument 22 is then pulled away from the plate 20 and the spacer 18 and the alignment prongs 48 are decoupled or disengaged from the slots 32 of the spacer 18. The alignment prongs 48 and the slots 32 generally do not lock to one another, but interface to provide tactile and visual feedback as to the positioning of the plate 20 with respect to the spacer 18. There is generally a gap G (FIG. 3) between the proximal end 26 of the spacer 18 and the distal surface 40 of the plate 20 once the plate 20 is fixedly attached to the vertebrae 12, 14 in the implanted configuration. The gap G is formed by a curvature of at least the distal surface 40 of the plate 20 to match the natural anatomy of the vertebrae 12, 14 proximate the disc space DS. The gap G is provided to prevent contact between the spacer 18 and the plate 20, and is maintained by the stability of the spacer 18 within the disc space DS, i.e., the spacer 18 is fixed in position once implanted.

Figure 3:
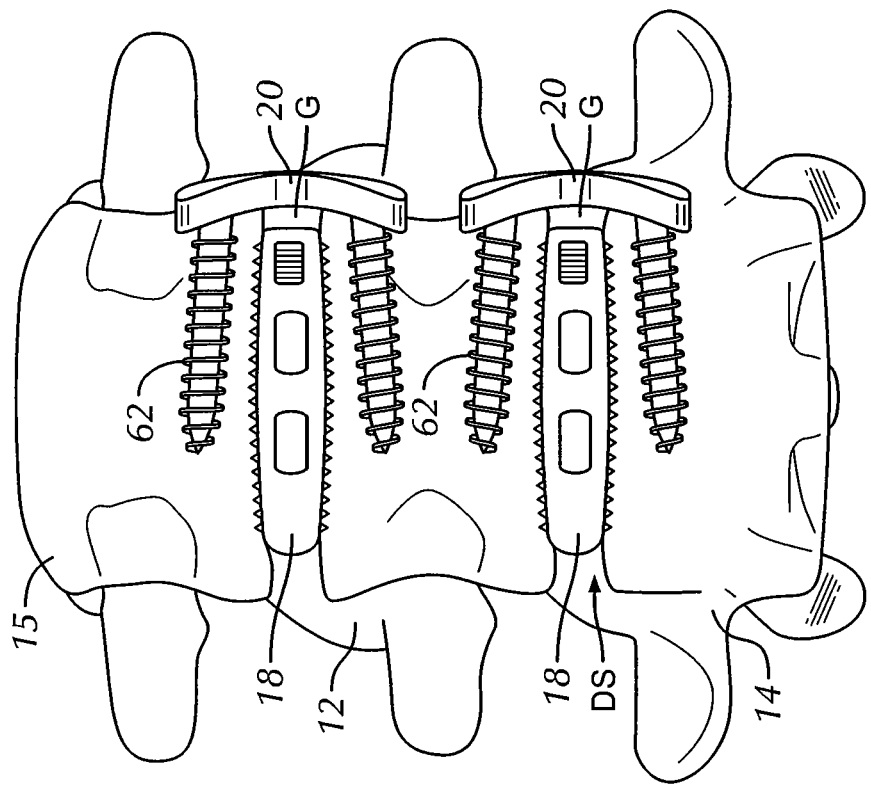
FIG. 3 is an anterior elevational view of two spaced-apart sets of a spacers, plates and anchors as shown in FIGS. 1-2 in a two level arrangement.
Figure 2:
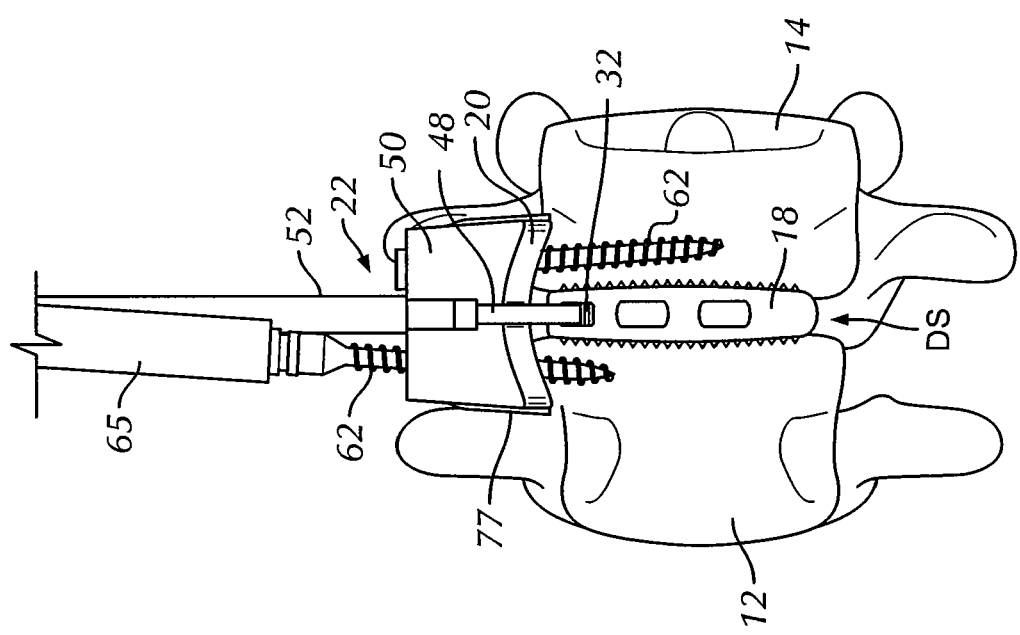
FIG. 2 is a magnified anterior elevational view of a portion of FIG. 1, which is similar to FIG. 1A, but shows screws being inserted therein to fix the plate to the vertebrae.

As seen in FIG. 3, the system 10 may include two ore more spaced-apart spacers 18 (i.e., a first spacer and a second spacer) positioned within the vertebral column and spaced therefrom, shown as a two-level surgery in FIG. 3. The two spacers 18 may be substantially identical, such that either spacer 18 may be interchanged in a disc space DS without affecting the function and operability of the system 10. The system 10 may also include two or more spaced-apart plates 20 (i.e., a first plate and a second plate), of which the first plate 20 is fixedly attached to the superior and inferior 12, 14 vertebrae and the second plate 20 is fixedly attached to the superior vertebra 12 and a vertebra 15 adjacent the superior vertebra 12 opposite the inferior vertebra 14 in the implanted configuration near a proximal end 26 of the second spacer 18. In the present embodiment, the two plates 20 are substantially identical, such that either plate 20 may be interchanged without affecting the function and operability of the system 10. The system 10 may alternatively utilize a single two-level plate as would be apparent to one having ordinary skill in the art.

Furthermore, the system 10 may include two or more separate aiming devices 50 (i.e., a first aiming device and a second aiming device) that are each removably mountable to one of the two plates 20, such that the first and third screw alignment bores 56a, 56b of the second aiming device 50 are aligned with superior and inferior screw holes 34, 36 of the second plate 20, respectively, when the second aiming device 50 is mounted to the second plate 20. Each aiming device 50 typically includes the guide groove 58. The two aiming devices 50 may be substantially identical, such that either aiming device 50 may be interchanged with one or more alignment instruments 22 without affecting the function and operability of the system 10.

Figure 5:
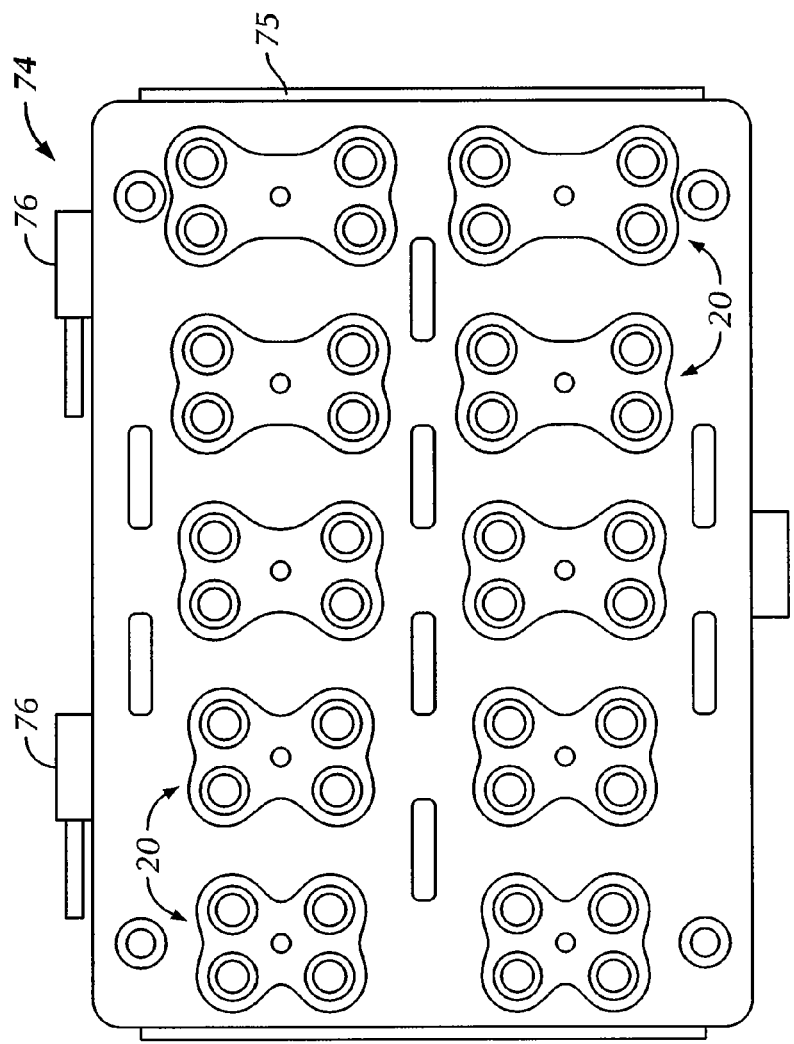
FIG. 5 is a top plan view of a kit for holding various sized plates similar to the plate shown in FIGS. 1-4.
Figure 7:
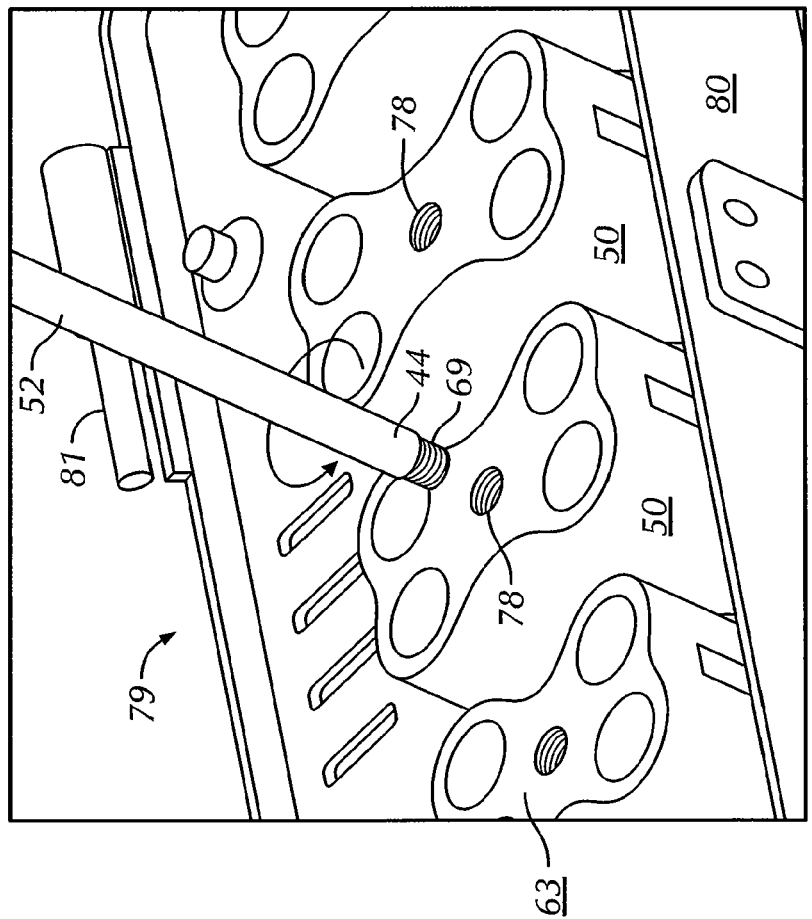
FIG. 7 is a magnified side isometric view of a portion FIG. 6 including the alignment instrument and several of the aiming devices.
Figure 6:
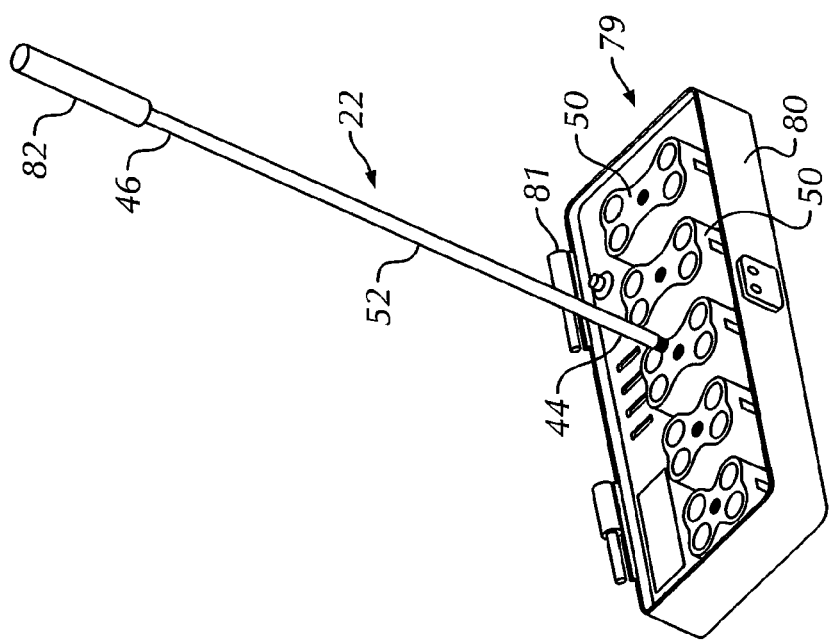
FIG. 6 is a side isometric view of a shaft of the alignment instrument proximate an aiming device of the alignment instrument in a kit for holding various sizes of the aiming devices.

As seen in FIG. 5, the system 10 may include a plate kit including a plate case 74 for storing and/or transporting, for example, at least two and potentially a plurality of plates 20 of varying size and/or shape. In the present embodiment, the plate case 74 is shown holding five pairs of plates 20, but the system 10 is not so limited. The plate case 74 includes a base 75 and a lid (not shown) to enclose the plates 20 therein. One or more hinges 76 may allow the lid to be pivotally attached to the base 75. In the first exemplary embodiment, the base 75 includes a top row having a series of depressions or cut-outs that increase in size and/or shape from a left side of the top row to a right side of the top row. Each cut-out is sized and shaped to generally hold or surround one plate 20, for example. Similarly, a lower row of the base 75 includes a series of depressions or cut-outs that are sized and shaped to generally surround one plate 20, for example. Although it is shown in this exemplary embodiment that the consecutive cut-outs hold or surround an incrementally sized and/or shaped plate 20, as compared to an adjacent cut-out, the plate case 74 is not so limited. Alternatively, the plate case 74 may include prongs (not shown) to secure the plates 20 therein Additionally or alternatively, as seen in FIGS. 6 and 7, the system 10 may include an aiming device kit including an aiming device case 79 for storing and/or transporting, for example, at least two and generally a plurality of aiming devices 50 of varying size and/or shape. In the present embodiment, the aiming device case 79 is shown holding five aiming devices 50 of increasing size and/or shape, but the system is not so limited. The aiming device case 79 includes a base 80 and a lid (not shown) to enclose the aiming devices 50 therein. One or more hinges 81 may allow the lid to be pivotally attached to the base 80. The base 80 may include a series of depressions or cut-outs that increase in size and/or shape from a left side of the base 80 to a right side of the base 80, in which each cut-out is sized and shaped to generally hold or surround one aiming device 50. Consecutive cut-outs generally hold or surround an incrementally sized and/or shaped aiming device 50, as compared to an adjacent cut-out, the aiming device case 78 is not so limited. Alternatively, a bottom interior surface of the base 80 may include one or more protrusions (not shown) that extend upwardly from the bottom interior surface and are sized and shaped to engage or surround at least a portion of each aiming device 50 to generally hold each aiming device 50 in place. The plate case 74 and aiming device case 79 may also be combined into a single case, that may also hold the remaining portions of the alignment instrument 22 and/or one or more spacers 18. The plate case 74, the aiming device case 79 and/or other components of the kit(s) are autoclaveable or adaptable to permit sterilization of the kit(s) following surgery.

Figure 13:
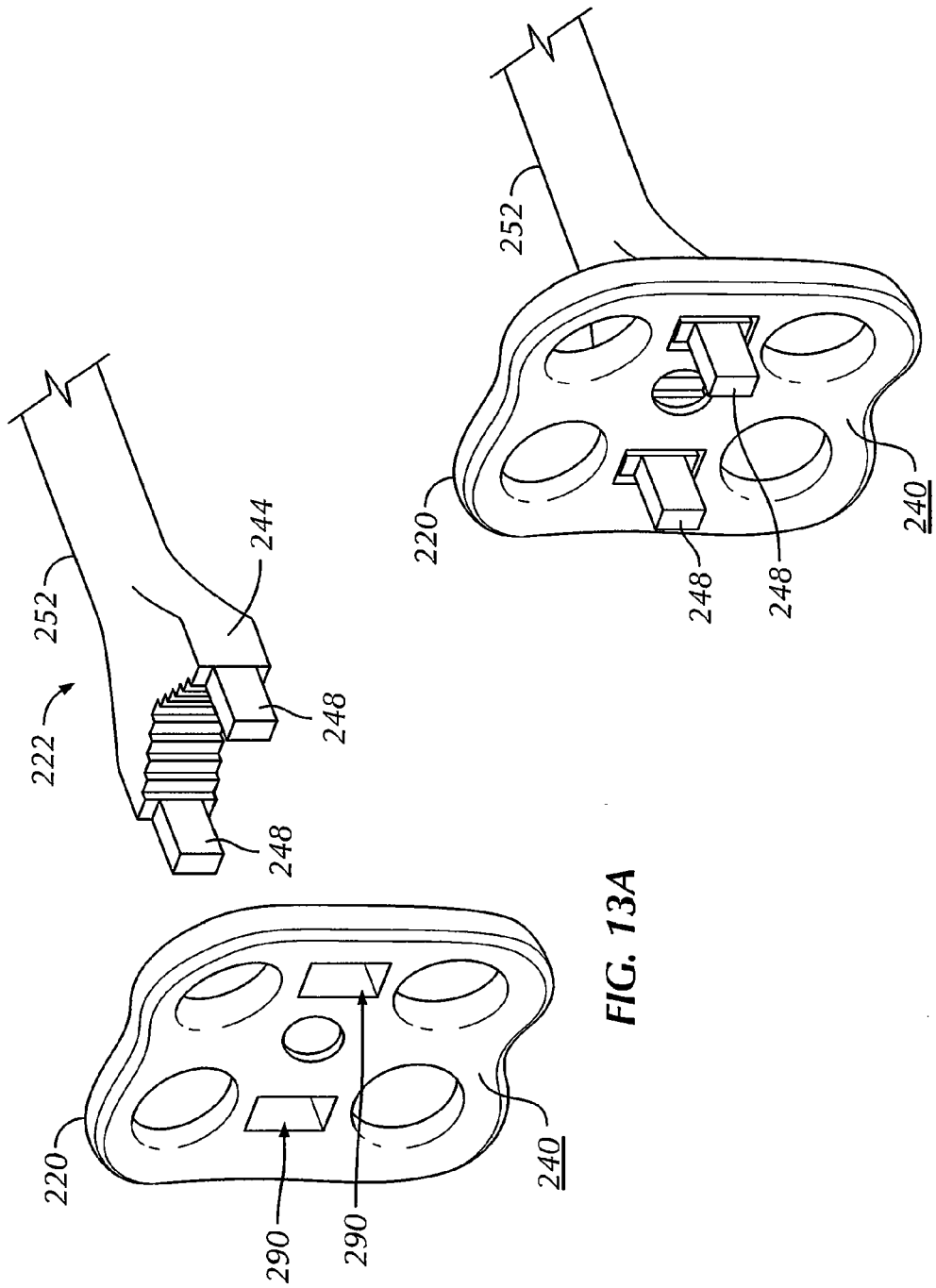
FIG. 13A is a side isometric view of the plate shown in FIG. 12 prior to be coupled with an alignment instrument in accordance with the second exemplary embodiment of the present application.
FIG. 13B is a side isometric view of the plate shown in FIGS. 12 and 13A coupled to the alignment instrument shown in FIG. 13A.
Figure 14:
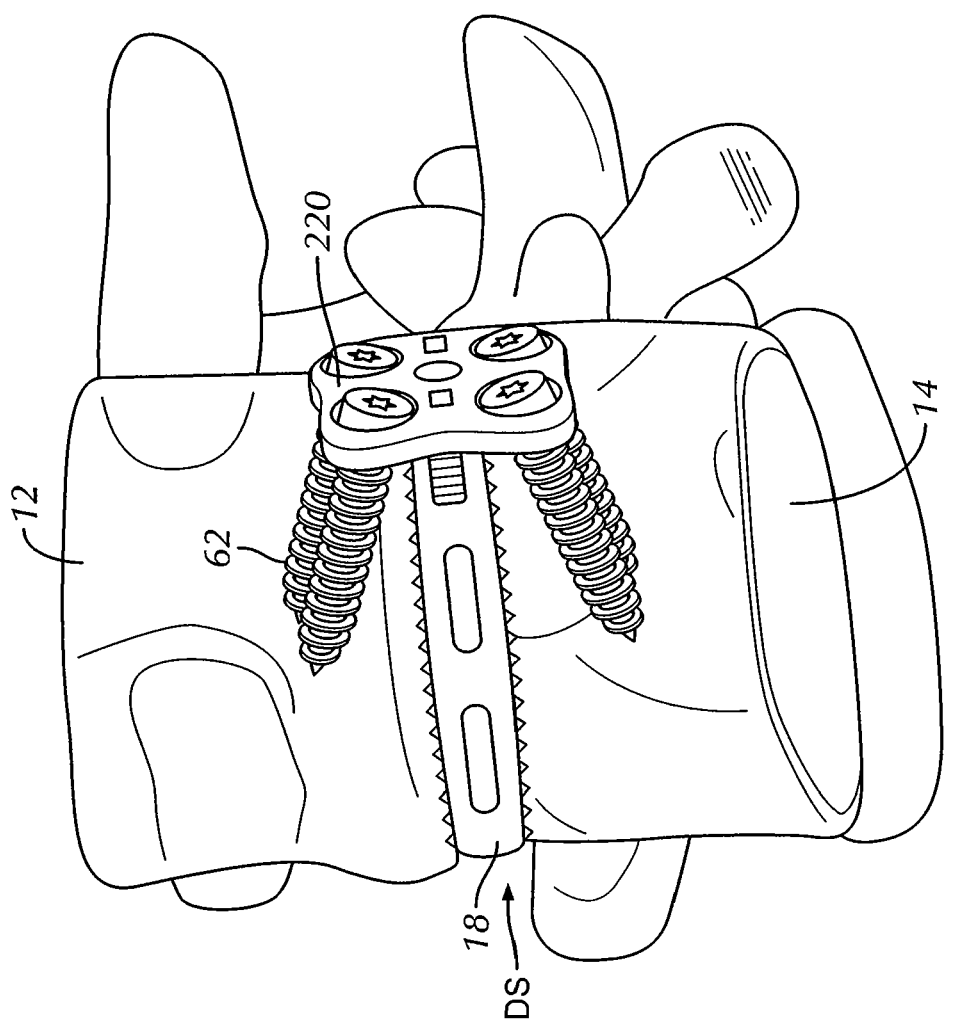
FIG. 14 is a side isometric view of the plate shown in FIGS. 12-13B shown in an implanted configuration for fixing the spacer between two adjacent vertebrae.

FIGS. 12-14 show a second exemplary embodiment of the plate, generally designated 220, and the alignment instrument, generally designated 222, wherein like referenced numerals are utilized to indicate like elements throughout the several views. The reference numerals of the second exemplary embodiment are distinguishable from those of the first exemplary embodiment by the prefix "2", but otherwise indicate the same elements as in the first exemplary embodiment, except as otherwise specified. The plate 220 and the alignment instrument 222 of the second exemplary embodiment are generally, if not substantially, similar to those of the first exemplary embodiment. For example, the plate 220 may include a proximal surface 238, an opposing distal surface 240, and at least one and a plurality of screw holes 234a, 234b, 236a, 236b. The plate 220 may include a centrally-located hole 235 that is threaded. Further, as seen in FIGS. 13A and 13B, the alignment instrument 220 includes a rod or shaft 252 that is removably attachable to the plate 220. Additional similarities between the first and second exemplary embodiments are omitted herein for the sake of brevity or convenience, and the omission thereof is not limiting.

In the second exemplary embodiment, the plate 220 includes a superior or first portion 242a, an opposite inferior or second portion 242b, and a middle portion or neck 242c located between the superior and inferior portions 242a, 242b. More specifically, the middle portion 242c is typically located between the superior screw holes 234a, 234b and the inferior screw holes 236a, 236b. In contrast to the first exemplary embodiment, the middle portion 242c has a width generally, if not exactly, equal to a width of the superior or inferior portions 242a, 242b. Thus, opposing sides of the plate 220 are generally straight or linear between the superior and inferior portions 242a, 242b. However, a superior side (i.e., top side) of the plate 220, proximate the superior portion 242a, and an interior side (i.e., bottom side) of the plate 220, proximate the inferior portion 242b, are at least generally curved, non-linear or concave. Thus, the plate 220 has a generally square shape when viewed from above or below (i.e., FIG. 12), but the plate 220 is not so limited.

As seen in FIGS. 12-13B, the plate 220 includes at least one and typically two-spaced apart throughholes 290. The throughholes 290 are proximate or within the middle portion 242c of the plate 220 and extend completely through the plate 220 from the proximal surface 238 to the distal surface 240. In the second exemplary embodiment, the throughholes 290 are each shown having a square or rectilinear cross-section and a cross-sectional area of each throughole 290 is shown as being less than that of any one of the screw holes 234a, 234b, 236a, 236b. However, the size and shape of the throughholes 290 may be modified. Further, the through holes 290 are located on opposing sides of the hole 235.

Referring specifically to FIGS. 13A and 13B, a distal end 244 of the shaft 252 of the alignment instrument 222 includes one or more engagement features, such as two spaced-apart alignment prongs 248. In the second exemplary embodiment, each prong 248 is sized and shaped to fit through or within one of the throughholes 290 of the plate 220 and engage or mate with a slot 32 of the spacer 18. Although each prong 248 is shown herein as having a rectangular shape, the prongs 248 are not so limited and may be formed in any size and shape that is capable of engaging a portion of the plate 220 (such as throughholes 290) and the spacer 18 (such as slot 32). Further, although not shown in the drawings, the concave shape of the superior and inferior sides of the plate 220 are sized to receive the extensions 77 of the aiming device 50 of the first exemplary embodiment. Thus, the plate 220 of the second exemplary embodiment may be used with either the alignment instrument 222 of the second exemplary embodiment or the alignment instrument 22 of the first exemplary embodiment.

Figure 16:
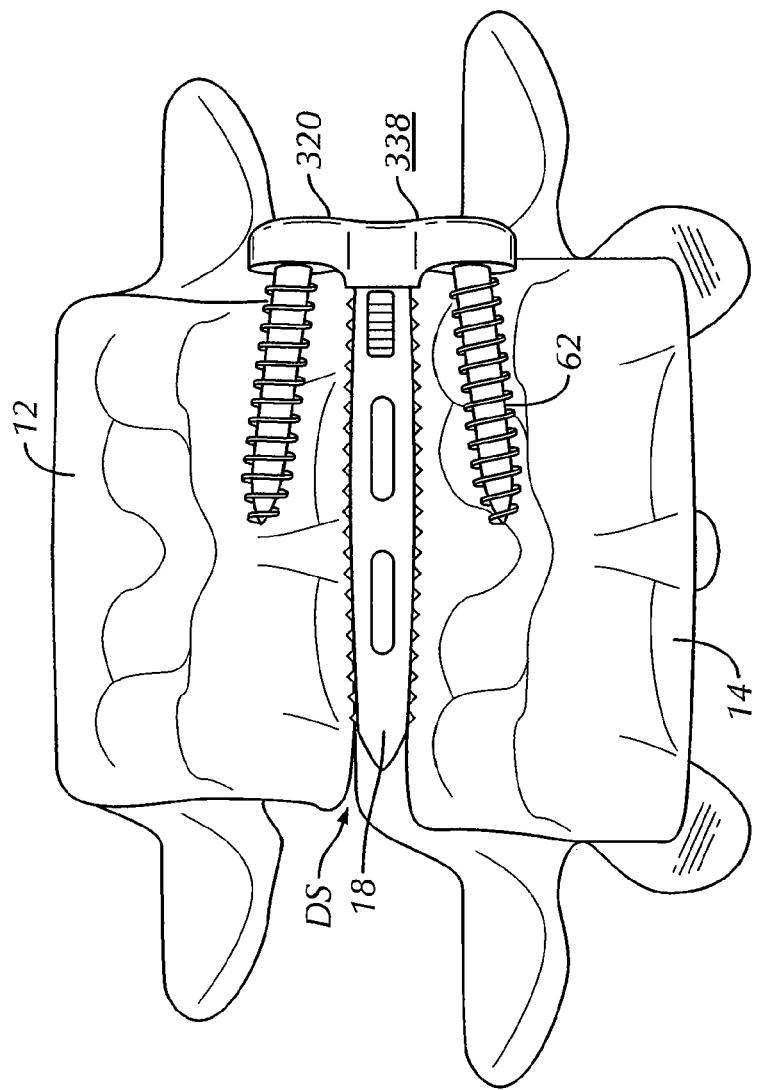
FIG. 16 is an anterior elevational view of the plate shown in FIG. 15 in an implanted configuration for fixing a spacer between two adjacent vertebrae.
Figure 15:
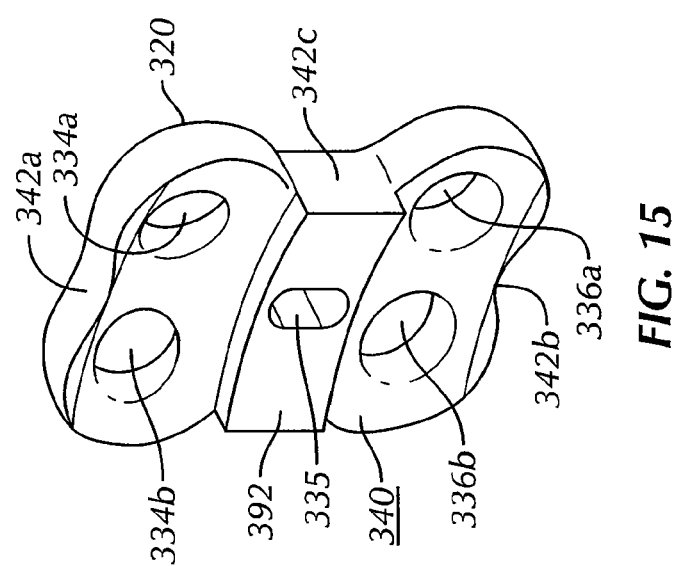
FIG. 15 is a bottom isometric view of a plate in accordance with a third exemplary embodiment of the present application.

FIGS. 15 and 16 show a third exemplary embodiment of the plate, generally designated 320, wherein like referenced numerals are utilized to indicate like elements throughout the several views. The reference numerals of the third exemplary embodiment are distinguishable from those of the first exemplary embodiment by the prefix "3", but otherwise indicate the same elements as in the first exemplary embodiment, except as otherwise specified. The plate 320 of the third exemplary embodiment is substantially similar to that of the second exemplary embodiment. For example, the plate 320 includes a proximal surface 338, an opposing distal surface 340, and at least one and generally a plurality of screw holes 334a, 334b, 336a, 336b. The plate 320 may also include centrally-located hole 335 that is threaded. Additional similarities between the third and second exemplary embodiments are omitted herein for the sake of brevity or convenience, and the omission thereof is not limiting.

Referring specifically to FIG. 15, the plate 320 includes a superior or first portion 342a, an opposite inferior or second portion 342b, and a middle portion 342c located at least between the superior and inferior portions 342a, 342b. More specifically, the middle portion 342c is located between the superior screw holes 334a, 334b and the inferior screw holes 336a, 336b. Similar to the first exemplary embodiment, the middle portion 342c has a smaller or narrower width than either the superior or inferior portions 342a, 342b and that opposing sides of the plate 320 have a generally smooth contour or shape defining a concave surface at the middle portion 342c between the superior and inferior portions 342a, 342b. Further, a superior side (i.e., top side) of the plate 320, proximate the superior portion 342a, and an interior side (i.e., bottom side) of the plate 320, proximate the inferior portion 342b, are generally slightly curved, non-linear or concave. However, the concave shape of the superior and inferior sides of the plate 320 are generally less pronounced or of a lesser degree than the concave shape of the opposing sides of the plate 320.

As shown in FIG. 15, the distal surface 340 of the plate 320 typically includes a tab 392 that extends or protrudes outwardly therefrom. In the third exemplary embodiment, the tab 392 extends generally across the entire width of the middle portion 342c of the plate 320 and completely surrounds the hole 335 on the distal surface 340. Further, in the present embodiment, the tab 392 extends outwardly from the distal surface 340 a uniform distance across the width of the middle portion 342c. The tab 392 is sized and shaped to locate the cranial and caudal aspects of the vertebral body endplate rims and position the plate 320 with respect to the spacer 18 relative to the disc space DS. While it is typical that the plate 320 is used in conjunction with the alignment instrument 22 of the first exemplary embodiment, the plate 320 is not so limited.

Figure 18:
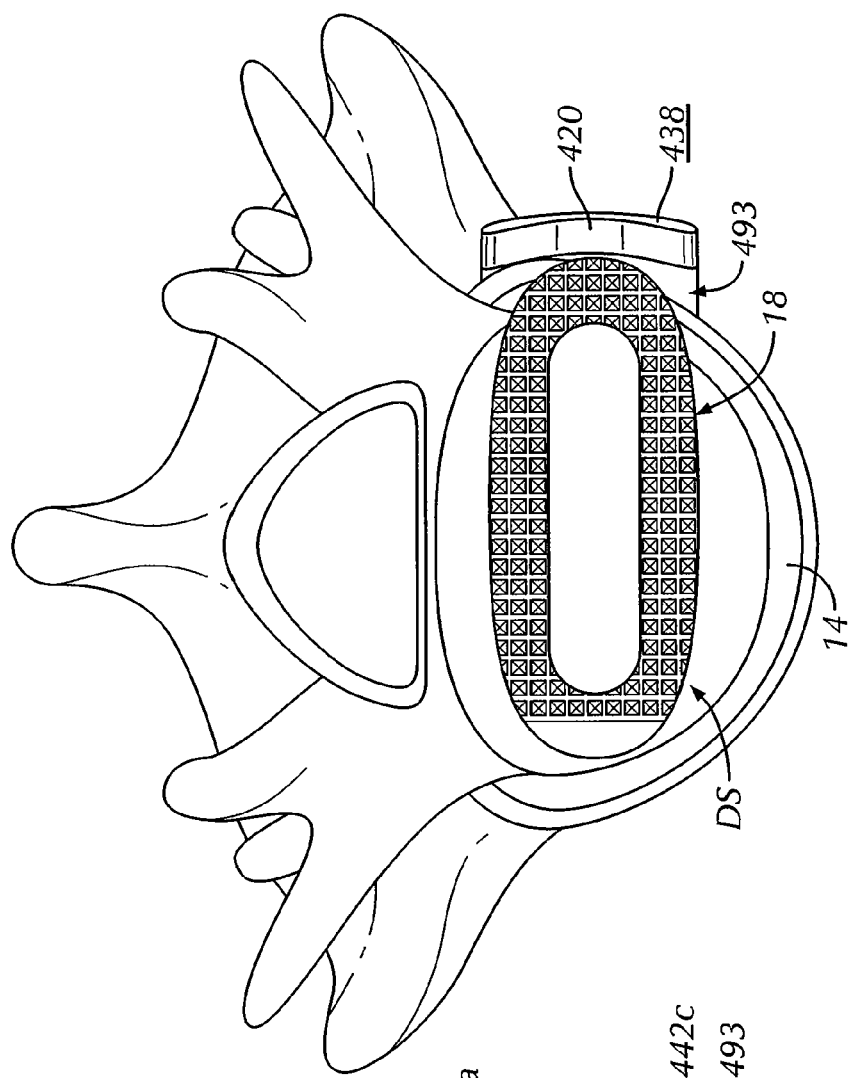
FIG. 18 is a cross-sectional, top plan view of the spacer of FIG. 10 and the plate of FIG. 17 in an implanted configuration for fixing the spacer between two adjacent vertebrae, with the screw(s) omitted for clarity.
Figure 17:
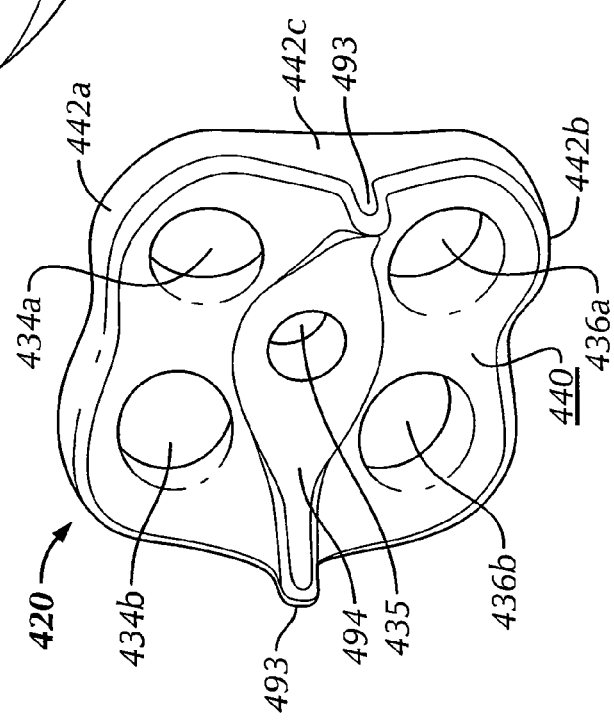
FIG. 17 is a bottom isometric view of a plate in accordance with a fourth exemplary embodiment of the present application.

FIGS. 17 and 18 show a fourth exemplary embodiment of the plate, generally designated 420, wherein like referenced numerals are utilized to indicate like elements throughout the several views. The reference numerals of the fourth exemplary embodiment are distinguishable from those of the first exemplary embodiment by the prefix "4", but otherwise indicate the same elements as in the first exemplary embodiment, except as otherwise specified. The plate 420 of the fourth exemplary embodiment is substantially similar to that of at least the second and third exemplary embodiments. For example, the plate 420 includes a proximal surface 438, an opposing distal surface 440, and at least one and potentially a plurality of screw holes 434a, 434b, 436a, 436b. The plate 420 may also include a centrally-located hole 435 that is threaded. Additional similarities between the fourth and second or third exemplary embodiments are omitted herein for the sake of brevity or convenience, and the omission thereof is not limiting.

In the fourth exemplary embodiment, the plate 420 includes a superior or first portion 442a, an opposite inferior or second portion 442b, and a middle portion 442c located at least between the superior and inferior portions 442a, 442b. More specifically, the middle portion 442c is generally located between the superior screw holes 434a, 434b and the inferior screw holes 436a, 436b. Similar to the second exemplary embodiment, the middle portion 442c has a width generally, if not exactly, equal to a width of the superior or inferior portions 442a, 442b. Thus, opposing sides of the plate 420 are generally straight or linear between the superior and inferior portions 442a, 442b. However, a superior side (i.e., top side) of the plate 420, proximate the superior portion 442a, and an interior side (i.e., bottom side) of the plate 420, proximate the inferior portion 442b, are at least slightly, generally curved, non-linear or concave.

As shown in FIG. 17, the distal surface 440 of the plate 420 includes at least one and typically two-spaced apart internal tabs 493 that are integrally formed with the plate 420. The tabs 493 extend axially from the distal surface 440 relative to an insertion direction and away from the distal surface 440. The tabs 493 are located on either side of a depression or concave area 494 that completely surrounds the hole 435 on the distal surface 440. The tabs 493 are generally located on or within the middle portion 442c and at opposing outer-most sides thereof. Further, in the fourth exemplary embodiment, each tab 493 includes an interior surface that defines a smooth or seamless transition to the concave area 494. The tabs 493 are generally sized and shaped to mate with the slots 32 on the proximal end 26 of the spacer 18 and the concave area 494 is sized and shaped to surround or engage at least a portion of the proximal end 26 of the spacer 18. The tabs 493 and concave area 494 are utilized to engage the spacer 18 to position and orient the spacer 18 and plate 420 relative to each other and the plate 420 relative to the vertebrae 12, 14. The plate 420 is generally used in conjunction with the alignment instrument 22 of the first exemplary embodiment, but is not so limited and may be utilized with alternative insertion instruments (not shown) for aligning the plate 420 with the spacer 18 and/or the patient's vertebrae 12, 14.

A method for stabilizing the superior vertebra 12 relative to the inferior vertebra 14 in spine surgery through the lateral access channel 16 includes inserting the spacer 18 into the disc space DS between the superior and inferior vertebrae 12, 14. The spacer 18 has the distal end 24 and the proximal end 26, the first side surface 28 and the second side surface 30, wherein the first side surface 28 has the slot 32 formed therein adjacent the proximal end 26, as described in detail above. The method further includes attaching a leading end 44, 244 of an alignment instrument 22, 222 to a plate 20, 220, 320, 420, an alignment prong 48, 248 extending outwardly from the leading end 44, 244 of the alignment instrument 22, 222 and beyond a distal surface 40, 240, 340, 440 of the plate 20, 220, 320, 420 when the leading end 44, 244 and the plate 20, 220, 320, 420 are attached. The alignment instrument 22 may include the aiming device 50, the removable shaft 52 and the locating guide 54, as described above. Further, the locating guide 54 may include the alignment prong 48 thereon. The method may also include inserting at least a portion of the removable shaft 52 into the opening 78, 71, 35 into each of the aiming device 50, the locating guide 54 and the plate 20 to align the aiming device 50 and the locating guide 54 with the plate 20.

In addition, the method typically includes using the alignment instrument 22, 222 to align the plate 20, 220, 320, 420 with respect to the spacer 18 by inserting at least a portion of the alignment prong 48, 248 into at least a portion of the slot 32 of the spacer 18. The method further includes inserting at least one screw 62 using a conventional screwdriver 65 (FIG. 2) or the like through the plate 20, 220, 320, 420 and into the superior vertebra 12 and inserting at least another screw 62 through the plate 20, 220, 320, 420 and into the inferior vertebra 14 to fixedly attach the plate 20, 220, 320, 420 to the superior and inferior vertebrae 12, 14. If necessary, temporary fixation screws (not shown) may be used to hold the plate 20, 220, 320, 420 in place while final preparation and screw 62 insertion is performed. Similarly, the cortical shell of the vertebrae 12, 14, 15 may be perforated using an awl (not shown) prior to screw 62 insertion. In order to tighten the screws 70 to a final position, the shaft 52, 252 of the alignment instrument 20, 222 may serve as a counter-torque handle.

The method also typically includes separating and withdrawing the leading end 44, 244 of the alignment instrument 22, 222 from the plate 20, 220, 320, 420. The method may also include removing the shaft 25 from the opening 35 in the plate 20 to separate the aiming device 50 and the locating guide 54 from the plate 20 and removing the alignment prong 48 from the slot 32 to allow withdrawal of the leading end 44 of the alignment instrument 22 from the plate 20.

It will be appreciated by those skilled in the art that changes could be made to the embodiments and/or method(s) described above without departing from the broad concept thereof. It is understood, therefore, that the above-described exemplary devices and methods are not limited to the particular embodiments and/or method(s) disclosed, but are intended to cover modifications within the spirit and scope of the exemplary embodiments as defined by the appended claims.

We claim:

1. A system for stabilizing a superior vertebra relative to an inferior vertebra, the superior vertebra and inferior vertebra having a spacer positioned therebetween, the system comprising:

a plate having a first surface configured for mating with the superior and inferior vertebra, a second surface generally opposite the first surface, and opposed exterior surfaces on an outer periphery of the plate, the opposed exterior surfaces extending between the first and second surfaces, the plate having a first hole that extends from the first surface to the second surface and a second hole that extends from the first surface to the second surface, the first and second holes being configured to simultaneously overlay the superior vertebra and the inferior vertebra, respectively, the plate further having a third hole disposed between the first surface and the second surface; and an alignment instrument having a leading portion and a trailing portion, the leading portion comprising a securing mechanism configured to be inserted into the third hole along an insertion direction so as to removably attach the alignment instrument directly to the plate, the alignment instrument further including an aiming device that is removably attachable to the leading portion, wherein the aiming device includes a guide groove, the alignment instrument further including a locating guide carrying a pair of opposed alignment prongs that are elongate along a first direction, the locating guide defining a base arm extending between the alignment prongs in a second direction that is perpendicular to the first direction, the base arm being sized and configured for insertion into the guide groove of the aiming device along the second direction such that an aperture of the base arm is aligned with the securing mechanism and configured to receive the securing mechanism, the alignment prongs extending axially from the leading portion of the alignment instrument such that the alignment prongs extend past the first surface of the plate so as to abut the opposed exterior surfaces when the plate is attached to the securing mechanism, the alignment prongs being configured to extend along the insertion direction into respective slots in the spacer, the alignment prongs providing tactile information to the trailing portion of the alignment instrument for use in positioning the plate with respect to the superior and inferior vertebra.

2. The system as recited in claim 1, wherein the alignment prongs extend approximately five to ten millimeters (5-10 mm) beyond the first surface of the plate when the plate is attached to the securing mechanism of the alignment instrument.

3. The system as recited in claim 1, wherein the alignment prongs of the alignment instrument are configured to mate with the respective slots.

4. The system as recited in claim 1, wherein the pair of opposed alignment prongs comprises first and second alignment prongs each extending approximately five to ten millimeters (5-10 mm) beyond the first surface of the plate when the plate is attached to the securing mechanism of the alignment instrument, the respective slots include first and second slots, and the first and second alignment prongs are configured to mate with the first and second slots, respectively, thereby aligning the plate with the spacer in at least two dimensions.

5. The system as recited in claim 4, wherein aligning the plate with the spacer further aligns the first hole for overlaying the superior vertebra and the second hole for overlaying the inferior vertebra.

6. The system as recited in claim 1, wherein the alignment instrument includes a shaft removably mountable to both the aiming device and the alignment prongs, such that the alignment prongs are detachably connected to the first aiming device.

7. The system as recited in claim 1, further comprising: a second aiming device with a second guide groove, the base arm of the locating guide being selectively mountable in the guide groove and the second guide groove.

8. The system as recited in claim 1, wherein the alignment instrument includes a removable shaft, where the alignment prongs include a first alignment prong and a second alignment prong.

9. The system as recited in claim 1, wherein the first hole comprises first and second screw holes and the second hole comprises third and fourth screw holes, the plate including a neck between the first and second screw holes.

10. The system as recited in claim 9, wherein:
the aiming device includes first, second, third and fourth alignment bores, and a removable shaft; and
the first, second, third and fourth alignment bores are aligned with the first, second, third and fourth screw holes in an insertion position.

11. The system as recited in claim 10, wherein the alignment prongs include first and second alignment prongs, the first and second alignment prongs positioned adjacent a neck of the plate in the insertion position.

12. The system as recited in claim 1, wherein the first surface of the plate is spaced from the spacer when the spacer is in an implanted position.

13. The system of claim 1, further comprising:
the spacer having a distal portion, a proximal portion spaced from the distal portion along the insertion direction between the superior vertebra and the inferior vertebra, a first side surface that extends between the proximal portion and the distal portion, and a second side surface that is opposite the first side surface and extends between the proximal portion and the distal portion, the spacer having a slot disposed in the first side surface, the slot disposed adjacent the proximal portion.

14. The system of claim 13, wherein the spacer has a spacer length measured from the proximal portion to the distal portion and a spacer width measured from the first side surface to the second side surface, the spacer length being greater than the spacer width.

15. The system of claim 1, wherein the third hole includes two throughbores disposed between the first and second surface, and wherein the alignment prongs include first and second alignment prongs, the first and second alignment prongs configured to be received in the two throughbores so as to removably couple the alignment instrument directly to the plate.

16. A method for stabilizing a superior vertebra relative to an inferior vertebra in spine surgery through a lateral access channel, the method comprising the steps of
a) inserting a spacer along an insertion direction into a disc space between the superior and inferior vertebrae, the spacer having a distal end and a proximal end, wherein the distal end is spaced from the proximal end in the insertion direction, the spacer including a first side surface and a second side surface, the first and second side surfaces defining slots formed therein adjacent the proximal end;
b) inserting a base arm of a locating guide into a guide groove of an aiming device of an alignment instrument, the locating guide carrying opposed alignment prongs and the base arm including an aperture that is configured to receive a securing mechanism at a leading portion of an elongated shaft of the alignment instrument;
c) inserting the leading portion through an opening in the aiming device of the alignment instrument, the opening being aligned with the aperture of the base arm, the aiming device defining first and second bores that extend therethrough, and subsequently inserting at least a portion of the leading portion into an opening in a plate, the plate having a first bone screw hole and a second bone screw hole, such that the first and second bores of the aiming device are aligned with the first and second bone screw holes of the plate;
d) inserting at least a portion of the alignment prongs past respective opposed exterior surfaces on an outer periphery of the plate and into at least a portion of the slots of the spacer along the insertion direction so as to align the plate with respect to the spacer in a predetermined orientation;
e) inserting a first bone screw through the first bore, through the first bone screw hole, and into the superior vertebra, and inserting a second bone screw through the second bore, through the second bone screw hole, and into the inferior vertebra to fixedly attach the plate to the superior and inferior vertebrae; and
f) separating and withdrawing the elongated shaft from the plate.

17. The method according to claim 16, wherein step f) further comprises:
f1) removing the elongated shaft from the opening in the plate to separate the aiming device and the locating guide from the plate and removing the alignment prongs from the slots of the spacer to allow withdrawal of the elongated shaft from the plate.

18. The method according to claim 16, wherein the removable shaft of step c) is threadably attached to the plate.

19. The method according to claim 16, wherein the alignment prongs of step e) further include first and second prongs and wherein the slots are comprised of a first slot on the first side surface and a second slot on the second side surface, wherein the first prong is positioned at least partially in the first slot and the second prong is positioned at least partially in the second slot.

20. The method according to claim 16, wherein the aiming device of step c) further includes a pair of extensions that are received at superior and inferior sides of the plate.

\* \* \* \* \*